United States Patent [19]
Jinbo et al.

[11] Patent Number: 6,075,607
[45] Date of Patent: Jun. 13, 2000

[54] METHOD FOR ESTIMATING DURABILITY OF OPTICAL MEMBER AGAINST EXCIMER LASER IRRADIATION AND METHOD FOR SELECTING SILICA GLASS OPTICAL MEMBER

[75] Inventors: Hiroki Jinbo, Yokohama; Norio Komine; Seishi Fujiwara, both of Sagamihara, all of Japan

[73] Assignee: Nikon Corporation, Tokyo, Japan

[21] Appl. No.: 09/166,528

[22] Filed: Oct. 6, 1998

[30] Foreign Application Priority Data

Oct. 7, 1997 [JP] Japan ..................................... 9-274200

[51] Int. Cl.$^7$ ................................................... G01B 11/00
[52] U.S. Cl. ........................... 356/388; 356/318; 356/36; 356/436
[58] Field of Search ............................. 356/388, 36, 318, 356/436

[56] References Cited

U.S. PATENT DOCUMENTS 5,673,114  9/1997  Ushio ....................................... 356/432

FOREIGN PATENT DOCUMENTS 10-019727  1/1998  Japan .

OTHER PUBLICATIONS

Itoh et al., *Laser–Induced Damage Threshold and Absorption Measurements In Rare–Gas–Halide Excimer Laser Components*, Optics Communications, 74 (1989) Dec. 15, No. 3/4, Amsterdam, NL, pp. 219–230.

P. Karlitschek, *Photodegradation and Nonlinear Effects in Optical Fibers Induced by Pulsed UV–Laser Radiation*, Optics Communications, 116 (1995) Apr. 15, Nos. 1–3, Amsterdam, NL, pp. 219–230.

*Primary Examiner*—Frank G. Font
*Assistant Examiner*—Reginald A. Ratliff
*Attorney, Agent, or Firm*—Morgan, Lewis & Bockius LLP

[57] ABSTRACT

A method is provided for estimating durability of an optical member against pulsed excimer laser beam irradiation. The method includes the steps of (a) irradiating a test sample for the optical member with a pulsed excimer laser beam to induce changes in transparency of the test sample with respect to the pulsed excimer laser beam, the irradiation being performed for such a time period as to cover not only a linear region and a saturation region and (b) measuring changes in the transparency of the test sample with respect to the pulsed excimer laser beam as a function of the cumulative number of the excimer laser pulses that have irradiated the test sample in step (a). The method further includes the step of (c) repeating steps (a) and (b) with a plurality of different first predetermined energy densities of the pulsed excimer laser beam to derive a correlation equation representing the changes in the transparency of the test sample in the linear region and the saturated region in terms of the energy density of the pulsed excimer laser beam and the cumulative number of the excimer laser pulses and (d) estimating the durability of the optical member under actual usage conditions using the derived correlation equation.

19 Claims, 8 Drawing Sheets

METHOD FOR ESTIMATING DURABILITY OF OPTICAL MEMBER AGAINST EXCIMER LASER IRRADIATION AND METHOD FOR SELECTING SILICA GLASS OPTICAL MEMBER

This application claims the benefit of Japanese Application No. 09-274200, filed in Japan on Oct. 7, 1997, which is hereby incorporated by reference.

BACKGROUND OF THE INVENTION

1. Field of the Invention

The present invention relates to a method for estimating deterioration of the optical member and the maximum pulse number that can be applied to the optical members, or optical lenses, such as illumination lenses and projection lenses for use in KrF (248 nm) or ArF (193 nm) excimer laser lithography and optical lenses for excimer laser processing apparatus or the like.

2. Discussion of the Related Art

For the photolithographic technology for exposing and transcribing fine patterns of integrated circuits onto wafers made of silicon, or the like, an exposure apparatus called a stepper has been used. Due to an increasing trend towards higher integration of LSI, the wavelength of the light source of the stepper has been becoming shorter and shorter; from the g-line to the i-line, and further to KrF and ArF excimer lasers. Conventional general-use optical glass can no longer be used for the illumination system or the projection lens of this type of excimer laser stepper. Thus, silica glass and fluorite have been used for the optical members of the excimer laser exposure apparatus, for example.

The silica glass and fluorite used for lenses of the illumination and projection systems processing excimer laser beams require, as in the case of conventional optical glass, a bulk transmittance of 99.5%/cm or more, or 99.8%/cm or more. Considerable amounts of research have been conducted to develop optical members having such a high transmittance in the ultraviolet range. Among others, optical deterioration in optical members; i.e., changes in optical properties of optical members over time caused by the properties of excimer laser light, such as short wavelengths and flashing nature of the laser beams (so-called solarization and compaction), has significant effect on the imaging performances. Therefore, this deterioration has been one of the major problems in developing suitable glass members, and it is important to investigate the behavior and causes of this optical deterioration.

In particular, in order to investigate the behavior of the deterioration of silica glass for use with an irradiation energy of 10 mJ/cm$^2$ per pulse or less, it is most desirable to measure changes in physical properties, such as the transmittance, refractive index, and the surface profile, after actually irradiating a test piece with a laser beam of an actual energy density. However, with such a low irradiation energy density, each change in the physical properties due to one irradiation pulse is extremely small. Therefore, in order to produce detectable changes in these physical properties, it is necessary to increase the number of irradiation pulses. (In other words, the measurement period needs to be extremely long.) However, in reality, because of limited manpower and economic and temporal restrictions, it is difficult to keep on measuring one sample for several years. In addition, in the cases where stable performances need to be guaranteed over a decade or so, as in the case of reduction projection lenses made of expensive, special silica glass, such measurement is even more difficult.

Given these circumstances, there is a strong demand for developing a method of providing an accurate estimation of the life-span (estimation of durability) without actually measuring the deterioration (changes in the physical properties) in optical members over several years. Conventional estimation methods, which purport to achieve this goal, are effective only when the relationship between the reduction of the transmittance and the total number of irradiating pulses are linearly related. Thus, the conventional estimation methods are only applicable to estimation of the durability for a very low energy range, as may often be the case for the durability test of projection lenses. However, for illumination systems, when changes in transmittance, which occur due to irradiation of pulses of 1×10$^9$ pulses or more at an energy density of several mJ/cm$^2$ per pulse to several tens of mJ/cm$^2$ per pulse, are in question, there is a non-negligible possibility that the reduction in transmittance may be grossly overestimated. Therefore, it has been difficult to accurately estimate the life-span of the optical members.

In addition, in order to estimate the life-span of an optical system of excimer laser steppers or apparatus processing excimer laser beams in general, it is necessary to derive reliable formulae representing changes in the properties of the lens material irradiated with the excimer laser. Accordingly, it is necessary to experimentally investigate the precise causes of the deterioration of silica glass or other optical member used in excimer laser optical member. Nonetheless, the published technical articles so far only show partial or qualitative results on this point, and very little research has been conducted to determine the reliable estimation formulae; concrete formulae and/or methodology, which can quantitatively provide reliable estimation, have never been presented.

Furthermore, in the case that the optical member is silica glass, if the transmittance decreases by 3%/cm or more, it has been assumed that this deterioration in optical performances of the silica glass be caused by heat. Thus, when it was necessary to prove that there is no deterioration due to heat, it was necessary to select a test sample having a transmittance reduction of 3%/cm or less.

SUMMARY OF THE INVENTION

Accordingly, the present invention is directed to a method for estimating durability of optical member against excimer laser irradiation and a method for selecting a silica glass optical member that substantially obviate the problems due to limitations and disadvantages of the related art.

An object of the present invention is to provide an accurate and simple estimation method for estimating the durability of an optical member against excimer laser irradiation.

Additional features and advantages of the invention will be set forth in the description that follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the present invention provides an estimation method for the durability of an optical member against irradiation by an excimer laser, the method including a first step, wherein in a linear range where a linear approximation is possible (i.e., where the correlation between the absorption coefficient of the optical member and the integrated pulse number of the irradiating excimer laser is linear), the correlation between the hydrogen density and/or chlorine density in the optical member and the absorption coefficient, and the correlations between the irradiation energy density as well as the integrated pulse value and the absorption coefficient are derived, when the excimer laser with a first designated irradiation energy density (for example, 0.01 to 10,000 mJ/cm$^2$ per pulse) irradiates the optical member, and then from these correlations, a first correlation equation for the absorption coefficient with the hydrogen density and/or chlorine density as well as the irradiation energy density and the integrated pulse value in the linear range is determined; a second step, wherein in the saturated range, the saturated absorption coefficient of the optical member is taken into account, and the correlation between the saturated absorption coefficient and the irradiation energy density and the correlation between the hydrogen density and/or the chlorine density and the absorption coefficient, when an excimer laser with the first designated irradiation energy density irradiates the optical member are derived and from these correlations, a second correlation equation for the absorption coefficient with the hydrogen density and/or chlorine density as well as the irradiation energy density within the saturated range is determined; and a third step wherein by determining the changes in the absorption coefficient in the linear range, which can be obtained through substituting the hydrogen density and/or chlorine density in the optical member, the irradiation energy density and the integrated pulse value of the irradiating excimer laser in the first correlation equation, and finding the value of the absorption coefficient in the saturated range, which can be obtained through substituting the hydrogen density and/or chlorine density in the optical member, the irradiation energy density and the integrated pulse value of the irradiating excimer laser in the second correlation equation, then the changes in the transmittance of the optical member due to the excimer laser with the second designated irradiation energy density (actual condition for usage; for example, 0.00001 to 100 mJ/cm$^2$ per pulse) are determined so that the durability of the optical member is estimated.

In this process, the first correlation equation may be adjusted by a coefficient which is found statistically from the effects of the structural factors, fluorides, OH groups and the pulse width of the excimer laser. In addition, with this testing method of durability estimation against excimer laser irradiation, a silica glass optical member, with a 3%/cm or less change in transmittance for an excimer laser with respect to the second designated irradiation energy density (actual condition for usage, for example, 0.00001 to 100 mJ/cm$^2$ per pulse) can be selected.

In another aspect, the present invention provide a method for estimating durability of an optical member against pulsed excimer laser beam irradiation, the method including the steps of deriving a first correlation equation representing an absorption coefficient of a test sample for the optical member in terms of a first irradiation energy density of a pulsed excimer laser beam, the cumulative number of the excimer laser pulses that have irradiated the test sample, and at least one of hydrogen and chlorine concentrations in the test sample, the first correlation equation representing the absorption coefficient in a linear range where an absorption coefficient of the test sample increases with the cumulative number of the excimer laser pulses in a substantially linear manner, the step of deriving the first correlation equation including the steps of (a) deriving correlation between the absorption coefficient and the at least one of hydrogen and chlorine concentrations in the test sample, (b) deriving correlation between the absorption coefficient and the first irradiation energy density of the pulsed excimer laser beam, and (c) deriving the first correlation equation from the correlation derived in step (a) and the correlation derived in step (b); deriving a second correlation equation representing a saturated absorption coefficient of the optical member in terms of the first irradiation energy density of the pulsed excimer laser beam and at least one of the hydrogen and chlorine concentrations in the test sample, the second correlation equation representing the saturated absorption coefficient in a saturated region where the absorption coefficient is saturated to the saturated absorption coefficient after an arbitrary number of the excimer laser pulses irradiates the test sample, the step of deriving the second correlation equation including the steps of (d) deriving correlation between the saturated absorption coefficient and the first irradiation energy density of the pulsed excimer laser beam, (e) deriving correlation between the saturated absorption coefficient and the at least one of hydrogen and chlorine concentrations in the test sample, and (f) deriving the second correlation equation from the correlation derived in step (d) and the correlation derived in step (e); and estimating the durability of the optical member under actual pulsed excimer laser beam irradiation conditions, including the steps of (g) inputting a second irradiation energy density of the pulsed excimer laser beam to be actually directed towards the optical member and at least one of hydrogen and chlorine concentrations in the optical member into the first correlation equation to derive changes the absorption coefficient of the optical member in the linear region as a function of the cumulative number of pulses of the pulsed excimer laser beam having the second irradiation energy density, (h) inputting the second irradiation energy density of the pulsed excimer laser beam to be actually directed towards the optical member and the at least one of the hydrogen and chlorine concentrations in the optical member into the second correlation equation to derive a saturated absorption coefficient of the optical member in the saturated region, and (i) estimating the durability of the optical member against the pulsed excimer laser beam having the second irradiation energy density using changes the absorption coefficient derived in step (g) and the saturated absorption coefficient derived in step (h).

In another aspect, the present invention provides a method for estimating durability of an optical member against pulsed excimer laser beam irradiation, the method including the steps of (a) irradiating a test sample for the optical member with a pulsed excimer laser beam to induce changes in transparency of the test sample with respect to the pulsed excimer laser beam, the irradiation being performed for such a time period as to cover not only a linear region where the changes in transparency changes substantially linearly with the cumulative number of the excimer laser pulses, but also a saturation region where the changes in transparency are substantially saturated to a saturated value, which occurs after the linear region; (b) measuring changes in the transparency of the test sample with respect to the pulsed excimer laser beam as a function of the cumulative number of the excimer laser pulses that have irradiated the test sample in step (a), the measurement being conducted in both the linear region and the saturated region; (c) repeating steps (a) and (b) with a plurality of different first predetermined energy densities of the pulsed excimer leer beam to derive a correlation equation representing the changes in the transparency of the test sample in the linear region and the saturated region in terms of the energy density of the pulsed excimer laser beam and the cumulative number of the excimer laser pulses; (d) inputting the value of an energy density of the pulsed excimer laser beam corresponding to actual usage conditions of the optical member into the correlation equation to derive expected changes in the transparency of the optical member as a function of the cumulative number of the excimer laser pulses under the actual usage conditions; and (e) comparing the expected changes in the transparency derived in step (d) with a required transparency of the optical member to estimate the life-span of the optical member within which the optical member can satisfy the required transparency.

In a further aspect, the present invention provides a method for estimating durability of an optical member against pulsed excimer laser beam irradiation, the method including the steps of (a) irradiating a test sample for the optical member with a pulsed excimer laser beam to induce changes in transparency of the test sample with respect to the pulsed excimer laser beam, the irradiation being performed for such a time period as to cover not only a linear region and a saturation region; (b) measuring changes in the transparency of the test sample with respect to the pulsed excimer laser beam as a function of the cumulative number of the excimer laser pulses that have irradiated the test sample in step (a); (c) repeating steps (a) and (b) with a plurality of different first predetermined energy densities of the pulsed excimer leer beam to derive a correlation equation representing the changes in the transparency of the test sample in the linear region and the saturated region in terms of the energy density of the pulsed excimer laser beam and the cumulative number of the excimer laser pulses; and (d) estimating the durability of the optical member under actual usage conditions using the derived correlation equation.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1:
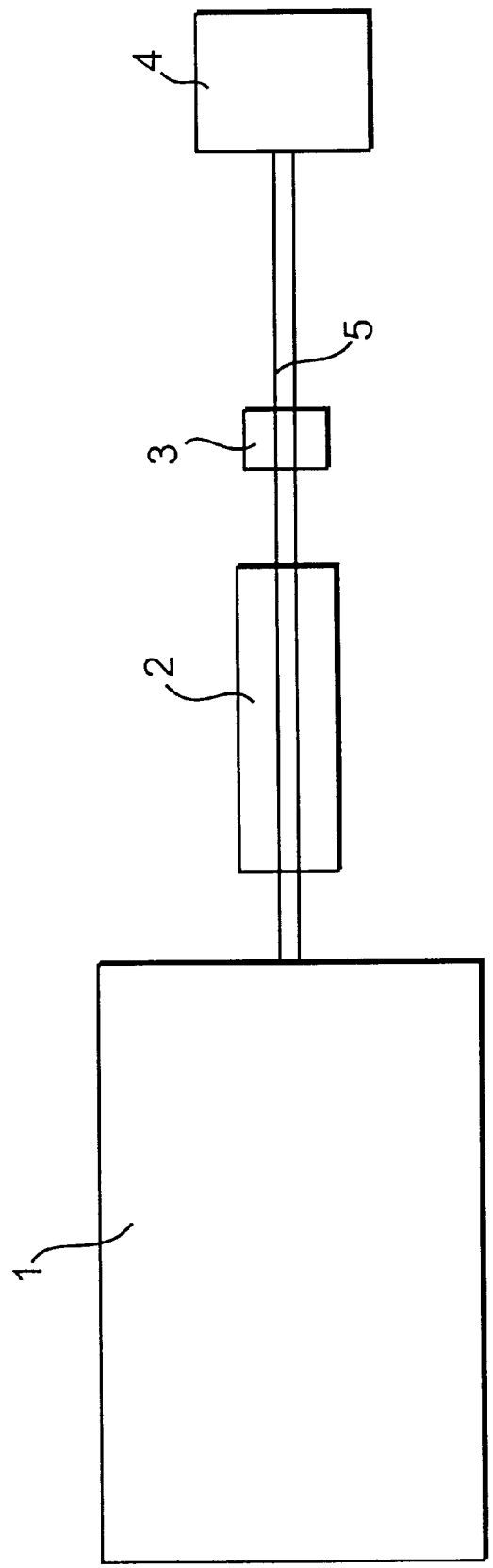
FIG. 1 is a schematic diagram showing an excimer illumination test apparatus used for deriving estimation formulae of the present invention.

FIG. 1 shows a measurement apparatus for excimer laser irradiation tests (life-cycle test). In this measurement apparatus, a homogenizer optical system 2, which also serves as a beam modifier, is disposed between ArF excimer laser light source 1 and an irradiated sample 3 (silica glass). Energy monitor 4 is disposed on the opposite side of ArF excimer laser light source 1 with respect to the sample 3. Laser beam 5 is generated from ArF excimer laser light source 1. The irradiation energy of the laser beam after it passes through the homogenizer optical system 2 and irradiation sample 3 is monitored by the energy monitor 4, and changes in the absorption coefficient of sample 3 are measured.

According to the present invention, in order to estimate the durability of an optical member against excimer laser irradiation, the following procedures are employed. First, using the measurement apparatus, test data are obtained by irradiating a test object of the optical member with excimer laser beams under various conditions. Then, based on the obtained test data, correlation equations representing the changes in the absorption coefficient are derived using statistical and theoretical methods. Finally, an estimation formula in the range where it is possible to make a linear approximation of the absorption coefficient with respect to the cumulative pulse number (linear range) and an estimation formula in the range where the absorption of the optical member is saturated (saturation range) are derived, and both formulae are combined.

When the irradiation energy density of the excimer laser irradiating the test sample to obtain the above-mentioned test data is in the range of about 0.01 to about 10,000 mJ/cm$^2$ per pulse, which is a preferable range for the measurement, the actual excimer laser irradiation energy density, which this accelerated test (life-cycle test) is designed to simulate, corresponds to the range of about 0.00001 to about 100 mJ/cm$^2$ per pulse. Accordingly, using the irradiation energy density in the range of about 0.01 to about 10,000 mJ/cm$^2$ per pulse for collecting the test data, it is possible to estimate the durability at a lower irradiation energy density of about 0.00001 to about 100 mJ/cm$^2$ per pulse.

Figure 2:
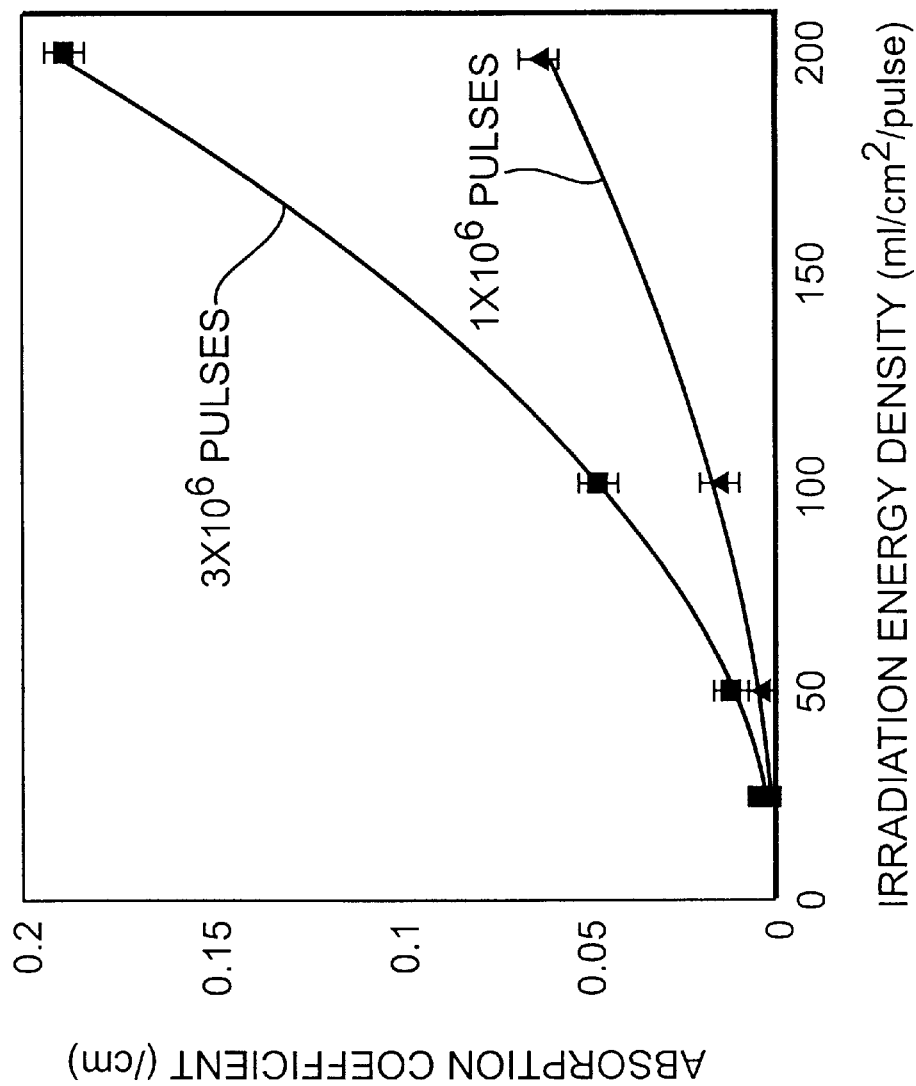
FIG. 2 shows dependency of the absorption coefficient of a silica glass at 193.4 nm on the energy density of an ArF laser beam in the linear range, which is used for deriving the estimation formulae of the present invention.

First, the absorption coefficient in the linear range obtained by the above-mentioned measurement system is described. FIG. 2 shows the measurement results indicating the dependency of the absorption coefficient on the irradiation energy, i.e., changes in the absorption coefficient ($cm^{-1}$) at 193.4 nm versus the irradiation energy density. Here, the same sample 3 was used and only the irradiation energy density was changed without changing other conditions. The irradiation energy density was set to be 25, 50, 100 and 200 ($mJ/cm^2$ per pulse). Then, the absorption coefficients at the cumulative pulse number of $1 \times 10^6$ pulses and $3 \times 10^6$ pulses were measured. (Often, the label "1E6" is used to represent "$1 \times 10^6$.") The density of the dissolved hydrogen in samples 3 was set to be $1 \times 10^{18}$ molecules/$cm^3$.

Equation (1) is a formula representing the dependency of the absorption coefficient on the energy density for sample 3 with respect to the ArF excimer laser irradiation, determined by the method of least squares based on these results:

$$\text{Absorption Coefficient (cm}^{-1}\text{) at 193.4 nm} = K_1 \cdot E^a, \quad (1)$$

where, E is the energy density ($mJ/cm^2$ per pulse), a is the dependency on the energy density: $a = 2 \pm 0.2$ ($3\sigma$), and $K_1$ is a constant.

The cause of the absorption band induced by an ArF or KrF excimer laser is a combined peak due to the E' center (215 nm band), $O_3$, and NBOHC (260 nm absorption band), which are created through two-photon absorption processes.

Figure 3:
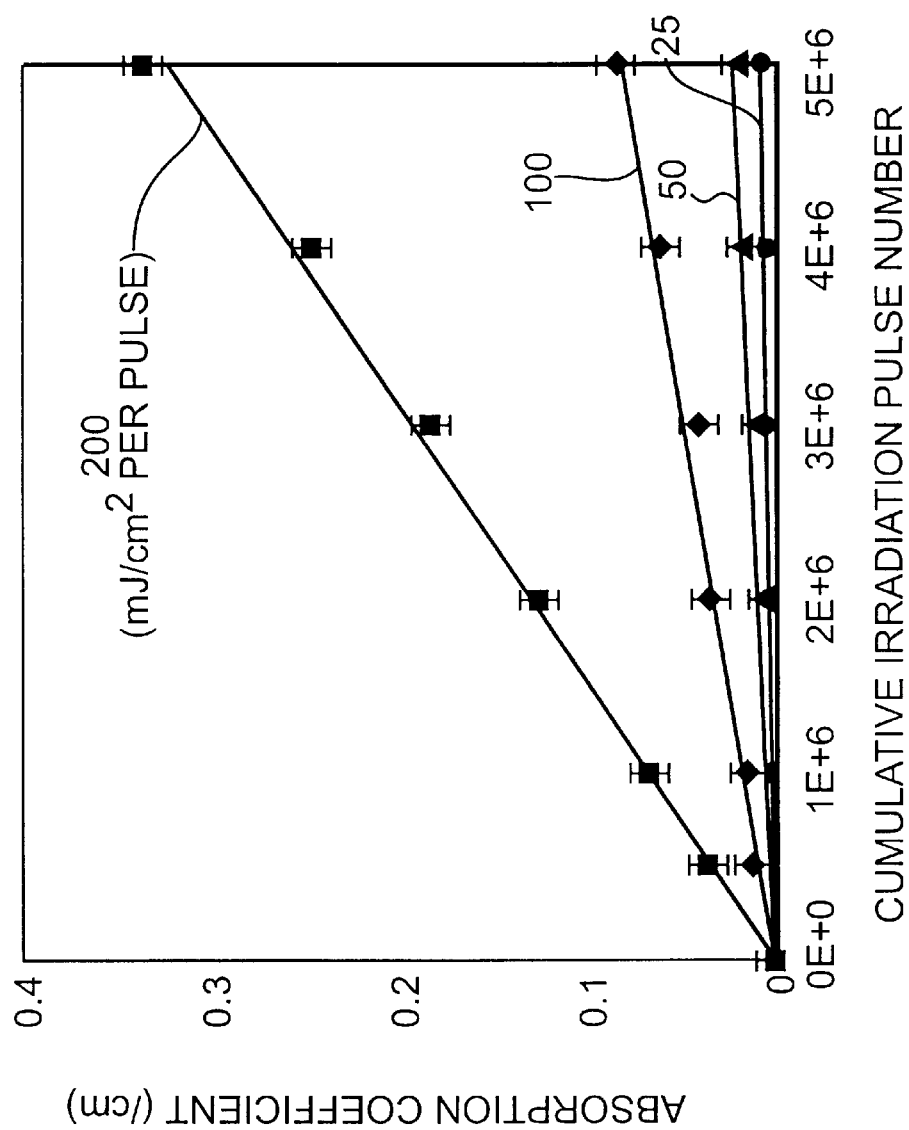
FIG. 3 shows the dependency of the absorption coefficient of the silica glass at 193.4 nm on the cumulative number of pulses of the ArF excimer laser beam in the linear range, which is used for deriving the estimation formulae of the present invention.

FIG. 3 shows the measurement results representing the dependancy of the absorption coefficient on the cumulative number of pulses, i.e., changes in the absorption coefficient ($cm^{-1}$) at 193.4 nm with respect to the cumulative pulse number. The irradiation energy density was set to be 25, 50, 100, and 200 $mJ/cm^2$ per pulse as a parameter, and the absorption coefficient at each of the plotted cumulative pulse number was measured, as shown in FIG. 3.

Equation (2) is a formula representing the dependency on the cumulative pulse number in the case of the ArF excimer laser irradiation, determined by the method of least squares based on is the results of FIG. 3.

$$\text{Absorption Coefficient (cm}^{-1}\text{) at 193.4 nm} = K_2 \cdot P^b, \quad (2)$$

where, P is the cumulative pulse number (pulses), b is the dependency on the cumulative pulse value: $b = 0.998 \pm 0.1$ ($3\sigma$), and $K_2$ is a constant.

This dependency formula holds only up to the absorption coefficient equal to or less than about 0.2 $cm^{-1}$. In the absorption coefficient range greater than that value, the dependency b on the cumulative pulse number gradually becomes smaller than 0.998 and eventually is saturated.

Figure 4:
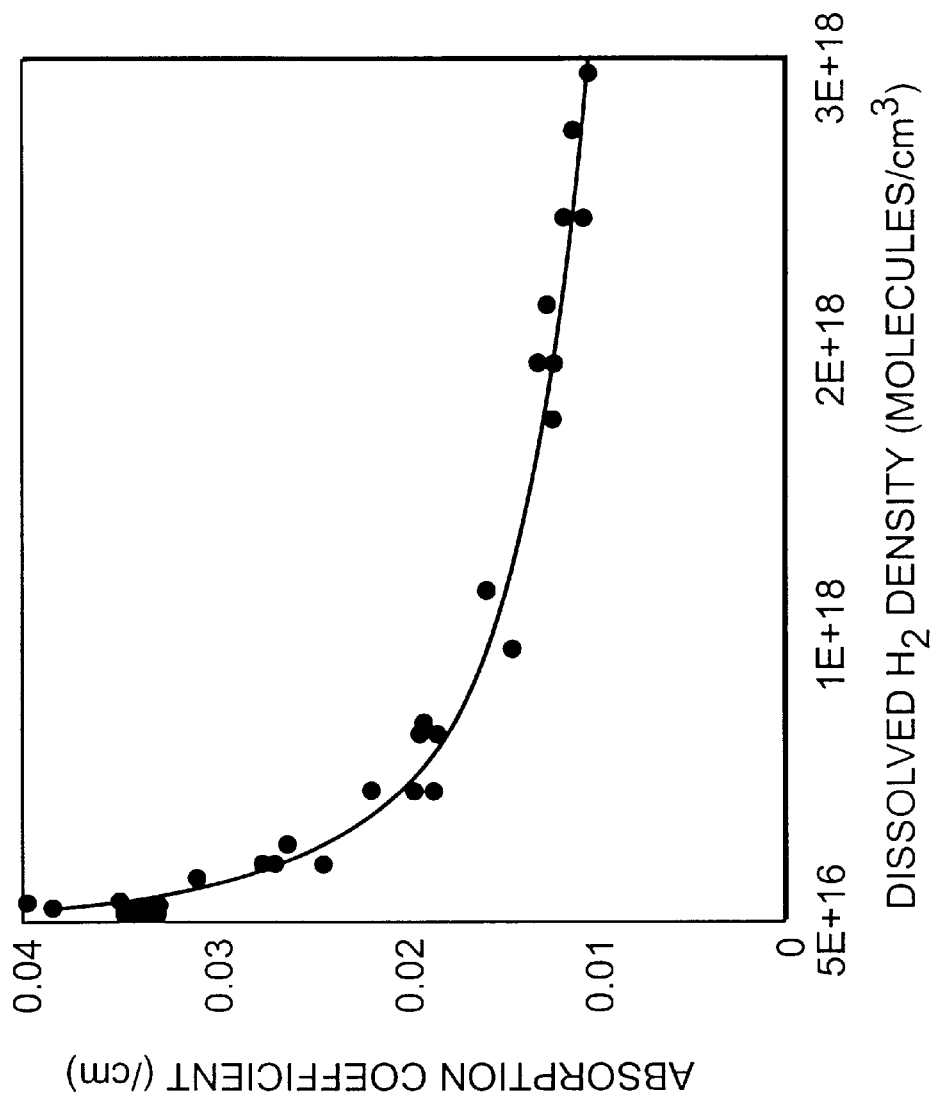
FIG. 4 shock the dependency of the absorption coefficient of the silica glass at 193.4 nm on the dissolve hydrogen molecule density in the silica glass in the linear range, which is used for deriving the estimation formulae of the present invention.

Next, the measurement results for the dependency of the absorption coefficient on the density of the dissolved $H_2$, i.e., changes in the absorption coefficient ($cm^{-1}$) at 193.4 nm with respect to the density of dissolved $H_2$ are described. FIG. 4 shows the correlation between the density of the dissolved $H_2$ (in the range of $5 \times 10^{16}$ to $3 \times 10^{18}$ molecules/$cm^3$) and the absorption coefficient ($cm^{-1}$) at 193.4 nm after the total (cumulative) pulse number of $1 \times 10^6$ is irradiated at an irradiation energy density of 100 $mJ/cm^2$ per pulse.

Equation (3) shows a formula representing the dependency determined by the method of least squares:

$$\text{Absorption Coefficient (cm}^-\text{) at 193.4 nm} = K_3 \cdot H^c, \quad (3)$$

where, H is the density of dissolved $H_2$ (molecules/$cm^3$), c is the dependency on the dissolved $H_2$ density, and $K_3$ is a constant. In Formula (3), c was determined to be $-0.38$ with the correlation coefficient r being 0.92. As evident from this high correlation coefficient value: $r = 0.92$, one of the dominant factors which affect the durability (namely the creation of absorption) of silica glass due to irradiation by an ArF excimer laser is the density of dissolved $H_2$ molecules.

As described above, from the above three formulas (1), (2) and (3), which show the absorption coefficient's dependency on the energy density, the cumulative number of pulses, and the dissolved $H_2$ density, respectively, an estimation formula for the absorption coefficient in the linear range for the sample 3 was determined as follows:

$$\text{linear Range Absorption Coefficient (cm}^{-1}\text{)} = K \cdot E^a \cdot P^b \cdot H^c \cdot d, \quad (4)$$

where, the constant K is $5.54 \times 10^{-6}$, a is $2 \pm 0.2$ ($3\sigma$), b is $0.998 \pm 0.1$ ($3\sigma$), and c is $-0.38 \pm 0.1$ ($3\sigma$). In Formula (4), d is a correction factor for a room temperature bleach phenomenon after the irradiation. If the transmittance is measured during the irradiation, then $d = 1$. The value of d increases exponentially with time after the irradiation, and for example, the d value 10 minutes after the irradiation becomes as much as 2.

At the ArF wavelength of 193.4 nm, the photon energy is 6.4 eV, which is significantly higher than that of 5 eV for the wavelength of 248.3 nm of a KrF excimer laser. Because of this and because the interband transition probability in the glass structure increases with increase in the photon energy, the Si—Cl bond is broken, and consequently, the probability of generating defects, such as the SiE' center, increases in the case of the ArF laser. Thus, the Si—Cl structure, which was not an issue in KrF excimer laser irradiation, has considerable effects on properties of silica glass under ArF excimer laser irradiation. Therefore, to estimate the durability against ArF excimer laser irradiation, it is necessary to find the dependency of the properties of the silica glass on the density of chlorine which is an undesirable impurity for durability.

An example of finding such a dependency on the chlorine density is next described. The correlation between the Cl density and the absorption coefficient ($cm^{-1}$) at 193.4 nm was studied for silica glass samples after the silica glass samples are irradiated with the cumulative number of pulses of $1 \times 10^6$ at an irradiation energy density of 200 $mJ/cm^2$ per pulse. Specifically, changes in the absorption coefficients in the linear range for a sample having a chlorine concentration of 50 ppm and a chlorine free silica glass sample were measured. The measured absorption coefficient for the sample having the Cl density of 50 ppm was approximately 1.3 times as many as that of the Cl free silica glass. Also, the performances of silica glass samples having other chlorine densities were examined, which revealed that up to an chlorine density of about 200 ppm, the dependency is linear. Equation (5) shows a formula representing the dependency of the absorption coefficient on the chlorine density, determined by the method of least squares based on these results:

$$\text{Absorption Coefficient (cm}^{-1}\text{) at 193.4 nm} = Z \cdot (1 + 0.006 \text{ Cl}), \quad (5)$$

where, Cl is the chlorine density in ppm and Z is the absorption coefficient of the chlorine free sample.

The correlation coefficient r was 0.90. As evident from this high value of the correlation coefficient, the chlorine density in the silica glass is considered to be one of the dominant factors that determine the durability (the generation of absorption) of the silica glass against ArF excimer laser irradiation.

As in the cases of Equations (1), (2), and (3) which describe the absorption coefficient's dependency on the energy density, the dependency on the cumulative pulse number, and the dependency on the dissolved $H_2$ density, respectively, coefficient Z in Equation (5), which is the formulae representing the dependency of the absorption coefficient on the Cl density, can be determined. Thus, it is possible to include the absorption coefficient's dependency on the Cl density in the estimation Equation (4).

In a similar manner, by applying statistical analyses to experimental data using formulae, it is possible to determine coefficients representing other factors, such as the fluorine density, the OH group density, a factor relating to the Si—O—Si primary structure, and the effect of the pulse width of an excimer laser beam. Such factors can be incorporated into Equation (4) as correction factors. For example, it was confirmed that the absorption effect is inversely proportional to the pulse width of an excimer laser beam.

So far, the estimations based on the above formulas are effective only in the range where the absorption coefficient increases linearly with the cumulative pulse number due to the excimer irradiation, i.e., in the range where the transmittance decreases linearly with the pulse number.

Figure 5:
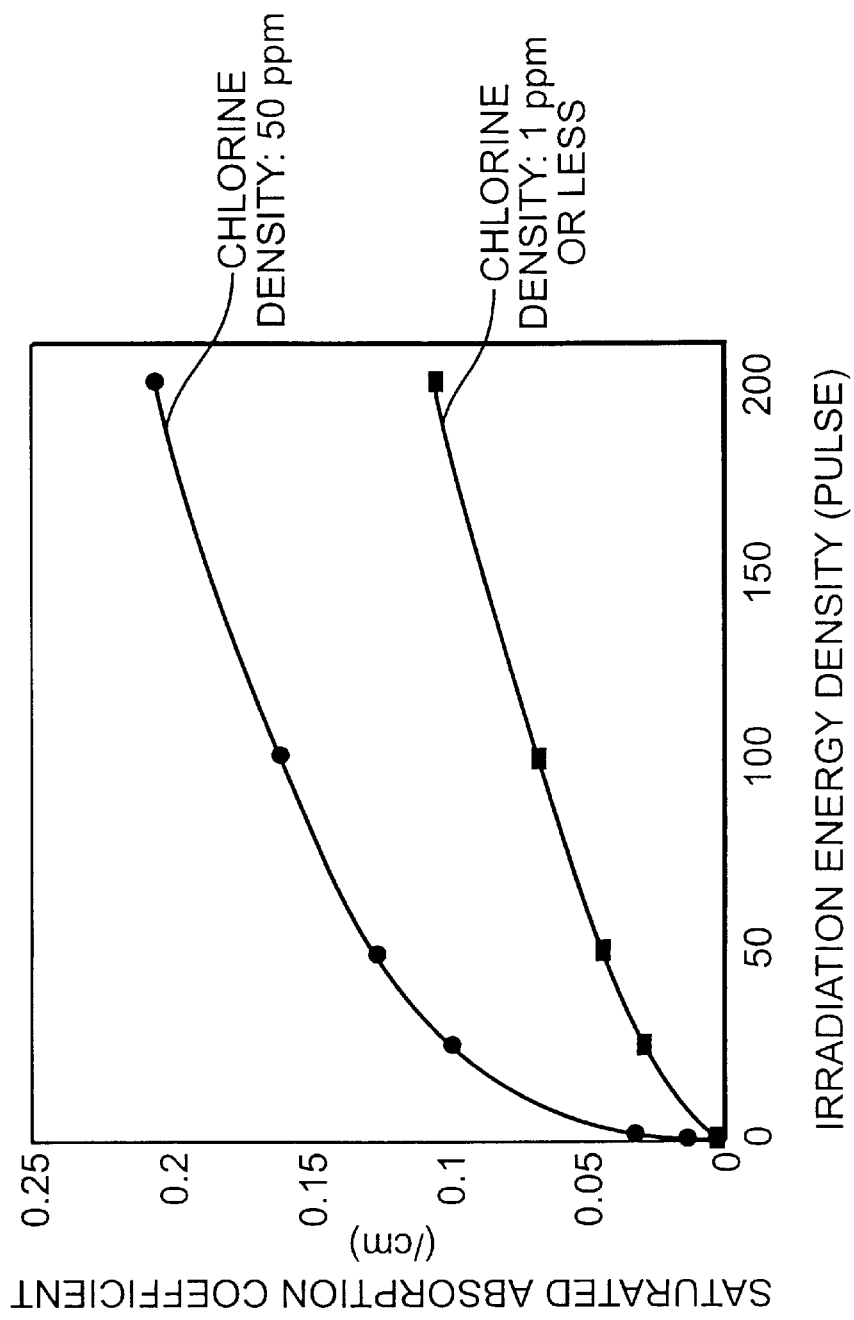
FIG. 5 show the dependency of a saturated absorption coefficient of the silica glass at 193.4 nm on the energy density of the ArF excimer laser beam with two different chlorine density in the silica glass, which is used for deriving the estimation formulae of the present invention.

Next, the absorption coefficient in the saturated range is described. The dependency of the saturated absorption coefficient on the irradiation energy density for an ArF excimer laser was examined. Using a dehydrogenized sample with a chlorine density of 50 ppm and a dehydrogenized sample with a chlorine density of 1 ppm or less, the dependency was measured at each of the irradiation energy densities 25, 50, 100 and 200 mJ/cm² per pulse. Excimer laser irradiation was carried out until the transmittance was saturated at each energy density. The results are shown in FIG. 5.

Figure 6:
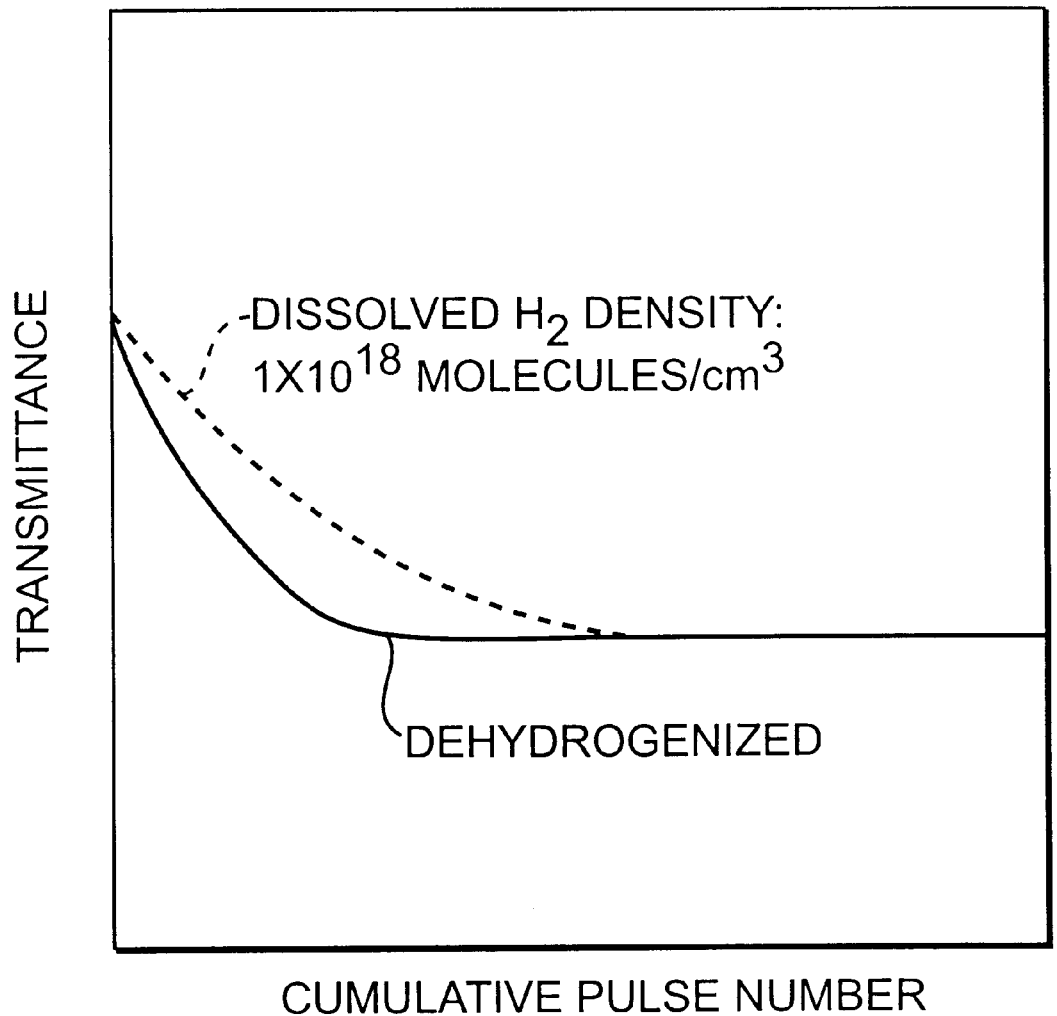
FIG. 6 shows the correlation between the cumulative number of pulses of the ArF excimer laser be am and the transmittance of silica glass for two silica glass samples having different molecular hydrogen densities, which is used for deriving the estimation formulae of the present invention.

Furthermore, the relationship between the cumulative pulse number and the transmittance changes was examined by using a sample having a molecular hydrogen density of $1 \times 10^{18}$ molecules/cm³ and a dehydrogenized sample. Both samples had a chlorine density of 50 ppm. The results are shown in FIG. 6. As shown in FIG. 6, the performance in the linear range up to the saturation value is different between the samples. Nonetheless, the saturation values are almost the same. This indicates that under ArF excimer laser irradiation, the dependency of the saturation absorption value on the hydrogen density is practically nonexistent. However, for a KrF laser, its saturation value depends on the hydrogen density because the absorption band is different from that for the ArF laser. Thus, in the case of using the KrF laser, it is necessary to incorporate this dependency into estimation of absorption in the saturation region. This can be achieved in a similar manner to the cases of estimating effects of other factors, which will be described below.

The dependency of the saturated absorption coefficient on the energy density was determined by the method of least squares based on data of FIG. 5, as follows:

$$\text{Absorption Coefficient (cm}^{-1}\text{) at 193.4 nm} = K_4 \cdot E^e, \quad (6)$$

The results are the same for both the dehydrogenized sample and the sample with a hydrogen molecule density of $1 \times 10^{18}$ molecules/cm³ under ArF excimer laser irradiation. Here, the dependency on the energy density e was $0.43 \pm 0.2$ (3σ). The value of $K_4$ depends on the chlorine density, as shown in FIG. 5, and may depend on the hydrogen molecule density for the case of KrF laser irradiation, as described above.

Figure 7:
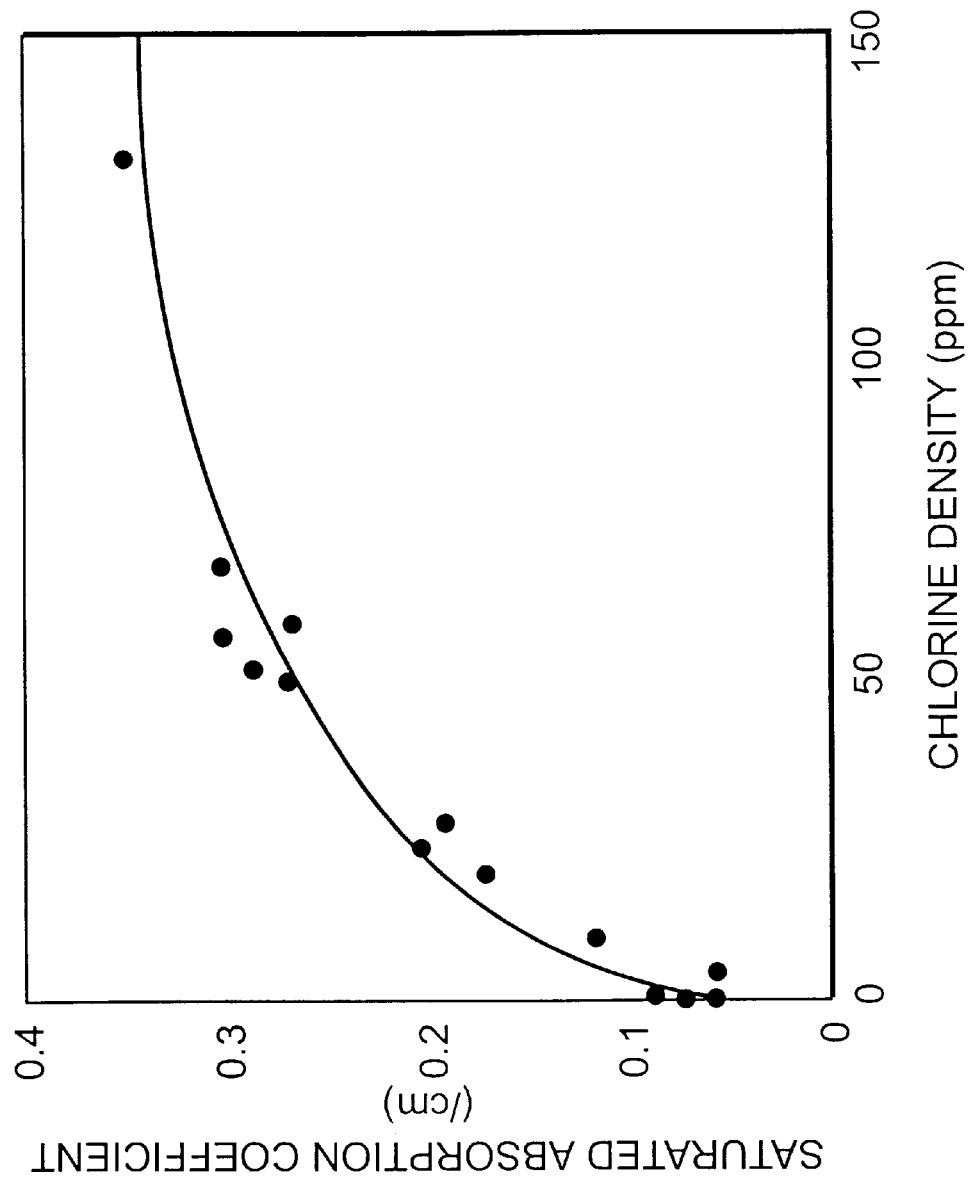
FIG. 7 shows the dependency of the saturated absorption coefficient of the silica glass at 193.4 nm on the chlorine density in the silica glass under ArF excimer laser irradiation, which is used for deriving the estimation formulae of the present invention.

Next, the dependency of the absorption coefficient on the chlorine density in the saturation region was investigated. For a dehydrogenized silica glass sample and silica glass samples with chlorine densities from 0 to 120 ppm, the dependency at an irradiation energy density of 200 mJ/cm² per pulse was studied. Excimer laser irradiation was carried out until the transmittance was saturated. The results are plotted in FIG. 7. Equation (7) shows a formula representing the dependency of the absorption coefficient on the chlorine density calculated by the method of least squares based on data shown in FIG. 7.

$$\text{Absorption Coefficient (cm}^{-1}\text{) at 193.4 nm} = K_5 \cdot (-2 \times 10^{-6} \text{ Cl}^2 + 5 \times 10^{-4} \text{ Cl} + 0.01), \quad (7)$$

where, Cl is the chlorine density in the silica glass in ppm and $K_5$ is a constant that depends on the energy density. By combining the above-mentioned formulae (6) and (7), the absorption coefficient can be expressed as Equation (8):

$$\text{Saturated Absorption Coefficient (cm}^{-1}\text{)} = K \cdot E^e (-2 \times 10^{-6} \text{ Cl}^2 + 5 \times 10^{-4} \text{ Cl} + 0.01) d, \quad (8)$$

where d is a correction factor for room temperature bleach phenomenon after irradiation, as described above.

Figure 8:
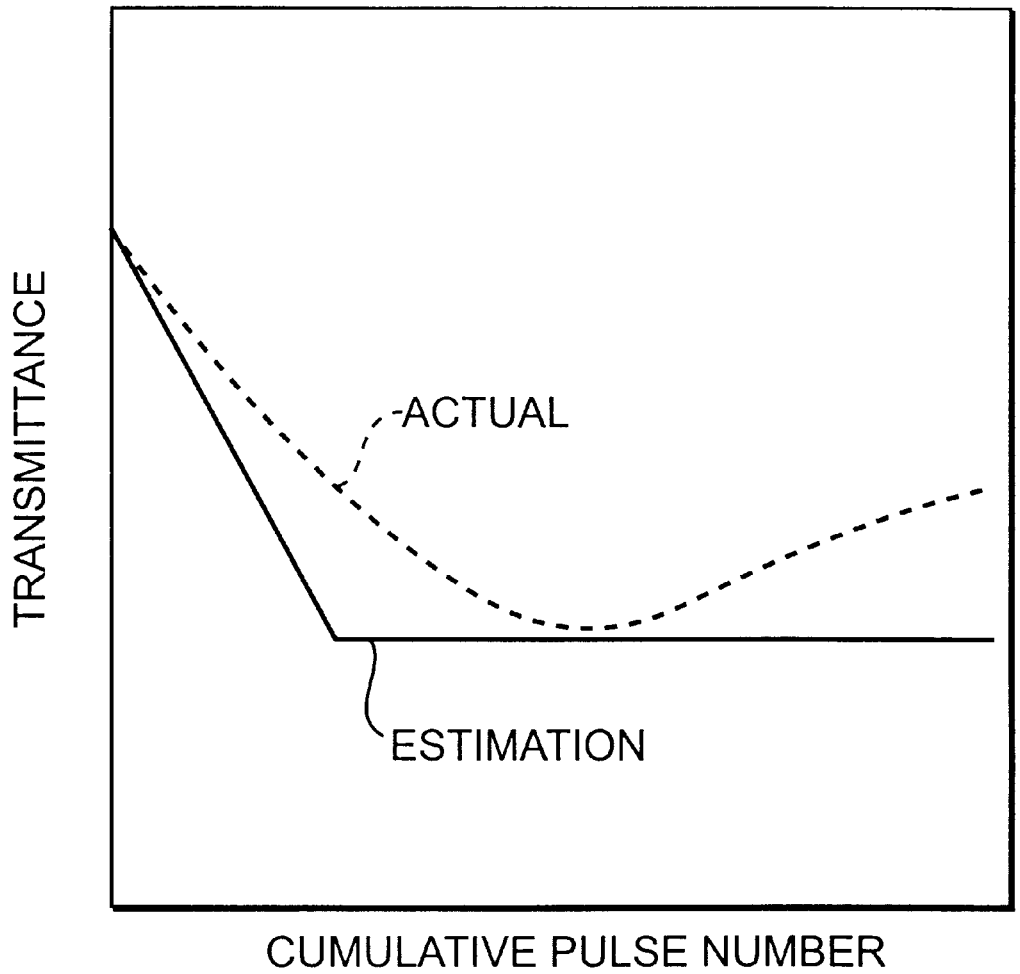
FIG. 8 shows changes in the transmittance of silica glass with respect to the cumulative number of pulses of the ArF excimer laser beam, estimated using the estimation formulae of the present invention, and the actually observed changes in transmittance.

Next, linear range formula (4) (or formula (4) with formula (5)) and saturated range formula (8) are combined. The solid line in FIG. 8 shows the transmittance obtained by Formula (4) (or (4)+(5)) and Formula (8). In the figure, the range where the transmittance decreases with the cumulative pulse number corresponds to the linear range and the range where the transmittance has a constant value corresponds to the saturated range. The dotted line in FIG. 8 shows the actual measured transmittance. As shown in FIG. 8, the transmittance is approximated such that it decreases with the cumulative pulse number and reaches the constant value after a certain number of pulses.

Various working examples are described below as preferred embodiments of the present invention. The optical member samples are cut out from a high purity silica glass ingot manufactured as follows. High purity silicon tetrachloride was used as the material, and oxygen gas and hydrogen gas were mixed and burned by a burner made of silica glass. The material gas was expelled from the center portion of the burner by diluting it with a carrier gas (normally, oxygen gas or hydrogen gas). The silica glass was then deposited and melted on a target plate. As a result, a silica glass ingot with a diameter of 180 mm and a length of 550 mm was obtained. First Preferred Embodiment (First Working Example)

Illumination optical lens parts for an ArF excimer laser stepper were produced by cutting the above-mentioned silica glass ingot. Also, samples for physical properties measurements were produced. The excimer laser irradiation test was carried out with respect to these samples to derive Formulae (4) and (8) for this case. The $H_2$ density of these optical silica glass parts was $1 \times 10^{18}$ molecules/cm³, and the Cl density was 20 ppm.

Typical conditions under which the illumination-use lenses are to be used (usage conditions) are: an irradiation energy density of 5 mJ/cm² per pulse and a repetitive frequency of 500 Hz. Assuming that the operating rate is 70%, the cumulative pulse number per day is $3 \times 10^7$ pulses, and the specification for the bulk absorption is 5%/cm or less. The expected transmittance behavior is calculated using Formula (9) with the absorption coefficient derived using estimation Formulae (4) and (8).

$$\text{Transmittance (\%)} = 100 \exp(-(\text{Absorption Coefficient}) \cdot \text{Thickness (cm)}) \quad (9)$$

Using this formula, the reduction in the bulk transmittance under the above-mentioned usage conditions was estimated to be −3.8%/cm. This value of the reduction in transmittance reached the saturated range, and therefore, it can be guaranteed that the specification (5%/cm or less) be met even if the cumulative number of pulses further increases. Thus, under these usage conditions, the saturated transmittance of the silica glass having the above quality was 96.2%/cm. The total transmittance for the entire optical system can be estimated by deriving the transmittance for each part and performing a simple multiplication.

Second Preferred Embodiment (Second Working Example)

Projection optical system-use lens parts for an ArF excimer laser stepper were produced by cutting a silica glass ingot. Also, samples for physical properties measurements were produced. The $H_2$ density of these optical silica glass parts was $1\times10^{18}$ molecules/cm$^3$, and the Cl density was 5 ppm. These lens parts are to be used in the projection optical system of the ArF excimer laser stepper, and the required specification for the internal absorption is 0.1%/cm or less.

Typical conditions under which the projection-use lenses are to be used (usage conditions) are: an irradiation energy density of 0.1 mJ/cm$^2$ per pulse and a repetitive frequency of 500 Hz. Assuming that the operating rate is 70%, the cumulative pulse number per day is $3\times10^7$ pulses.

Using the estimation formulae (4) and (8), the calculations were carried out in a similar manner to the first preferred embodiment. The reduction in the bulk transmittance under the above-mentioned usage conditions was estimated to be −0.1%/cm at $7\times10^{10}$ pulses. This result lies within the linear range, and therefore, the life-span of the lens was estimated to be about 6 years. Thus, it is possible to guarantee that the specifications will be satisfied for approximately 6 years. In addition, under these conditions of usage, it was estimated that the saturated transmittance of silica glass with the above quality is 99.5%/cm.

Third Preferred Embodiment (Third Working Example)

In a similar manner to the first and second embodiments, projection optical system-use lens parts for an ArF excimer laser stepper were produced by cutting a silica glass ingot. Also, samples for physical properties measurements were produced. The $H_2$ density of these optical silica glass parts was $2\times10^{18}$ molecules/cm$^3$, and the Cl density was 1 ppm or less. These lens parts are to be used in the projection optical system of the ArF excimer laser stepper, and the required specification for the internal absorption is 0.1%/cm or less.

Typical conditions under which the projection-use lenses are to be used (usage conditions) are: an irradiation energy density of 0.1 mJ/cm$^2$ per pulse and a repetitive frequency of 500 Hz. Assuming that the operating rate is 70%, the cumulative pulse number per day is $3\times10^7$ pulses.

Using the estimation formulae (4) and (8), the calculations were carried out in a manner similar to the first and second preferred embodiments. The reduction in the bulk transmittance under the above-mentioned usage conditions was estimated to be −0.1%/cm at $1\times10^{11}$ pulses. This result lies within the linear range, as in the second preferred embodiment, and the life-span of the lens was estimated to be about 10 years. Thus, it is possible to guarantee that the specifications will be satisfied for approximately 10 years. In addition, under these conditions of usage, it was estimated that the saturated transmittance of silica glass with the above quality is 99.6%/cm. If the specification for the bulk absorption can be relaxed to 0.2%/cm, the life-span of the lens would double.

In general, when a 3%/cm or more of the reduction in the transmittance of the optical member is generated, it may be assumed that the optical properties of the optical member have deteriorated due to heat. Using the estimation method of the present invention, it is possible to provide a silica glass which is guaranteed to have no deterioration in transmittance due to heat by proving that the reduction in the transmittance is 3%/cm or less.

As described above, by combining analyses in the linear range and the saturated range, it becomes possible to accurately and simply estimate changes in the transmittance of the silica glass optical member (i.e., the durability) without overestimating the reduction of the transmittance with respect to the cumulative pulse number.

In the above embodiments, examples with silica glass were presented. However, the present estimation method for durability can be used not only for silica glass but also for other optical members that are used for an excimer laser optical system. In addition, with this estimation method, it is possible to calculate the life expectancy and durability period of an excimer laser optical system. Furthermore, a similar estimation of the durability can be carried out with respect to other light sources or optical thin films. Also, using this estimation method, it is possible to select silica glass that has a decrease in the transmittance of about 3%/cm or less.

According to the estimation method of the present invention for durability against excimer laser irradiation, in addition to the changes in the absorption coefficient in the linear region where the relationship between the absorption coefficient and the cumulative pulse number can be approximated in a straight line, the saturated absorption coefficient of the silica glass optical member can be taken into account. Therefore, the overestimation of the reduction in the transmittance can be avoided and it is possible to accurately estimate the changes in the transmittance of a silica glass optical member (durability) in a relatively simply manner. In addition, by employing this method, it is possible to select silica glass that has a transmittance loss of about 3%/cm or less.

It will be apparent to those skilled in the art that various modifications and variations can be made in the method for estimating durability of optical member against excimer laser irradiation and a method for selecting silica glass optical member of the present invention without departing from the spirit or scope of the invention. Thus, it is intended that the present invention cover the modifications and variations of this invention provided they come within the scope of the appended claims and their equivalents.

What is claimed is:

1. A method for estimating durability of an optical member against pulsed excimer laser beam irradiation, the method comprising the steps of:

deriving a first correlation equation representing an absorption coefficient of a test sample for the optical member in terms of a first irradiation energy density of a pulsed excimer laser beam, the cumulative number of the excimer laser pulses that have irradiated the test sample, and at least one of hydrogen and chlorine concentrations in the test sample, the first correlation equation representing the absorption coefficient in a linear range where an absorption coefficient of the test sample increases with the cumulative number of the excimer laser pulses in a substantially linear manner, the step of deriving the first correlation equation including the steps of:
   (a) deriving correlation between the absorption coefficient and the at least one of hydrogen and chlorine concentrations in the test sample,
   (b) deriving correlation among the absorption coefficient, the first irradiation energy density, and the cumulative irradiation pulse number of the pulsed excimer laser beam, and (c) deriving the first correlation equation from the correlation derived in step (a) and the correlation derived in step (b);

deriving a second correlation equation representing a saturated absorption coefficient of the optical member in terms of the first irradiation energy density of the pulsed excimer laser beam and at least one of the hydrogen and chlorine concentrations in the test sample, the second correlation equation representing the saturated absorption coefficient in a saturated region where the absorption coefficient is saturated to the saturated absorption coefficient after an arbitrary number of the excimer laser pulses irradiates the test sample, the step of deriving the second correlation equation including the steps of:

(d) deriving correlation between the saturated absorption coefficient and the first irradiation energy density of the pulsed excimer laser beam, (e) deriving correlation between the saturated absorption coefficient and the at least one of hydrogen and chlorine concentrations in the test sample, and (f) deriving the second correlation equation from the correlation derived in step (d) and the correlation derived in step (e); and estimating the durability of the optical member under actual pulsed excimer laser beam irradiation conditions, including the steps of:

(g) inputting a second irradiation energy density of the pulsed excimer laser beam to be actually directed towards the optical member and at least one of hydrogen and chlorine concentrations in the optical member into the first correlation equation to derive changes the absorption coefficient of the optical member in the linear region as a function of the cumulative number of pulses of the pulsed excimer laser beam having the second irradiation energy density, (h) inputting the second irradiation energy density of the pulsed excimer laser beam to be actually directed towards the optical member and the at least one of the hydrogen and chlorine concentrations in the optical member into the second correlation equation to derive a saturated absorption coefficient of the optical member in the saturated region, and (i) estimating the durability of the optical member against the pulsed excimer laser beam having the second irradiation energy density using changes the absorption coefficient derived in step (g) and the saturated absorption coefficient derived in step (h).

2. The method according to claim 1, wherein step (i) includes the step of deriving the cumulative number of the excimer laser pulses up to which the absorption coefficient of the optical member is confined within a tolerable range using the changes in the absorption coefficient derived in step (g) and the saturated absorption coefficient derived in step (h).

3. The method according to claim 1, wherein the step of deriving the first correlation equation further includes the step of correcting the first correlation equation in accordance with a coefficient which is statistically derived to represent effects of structural factors of the test sample, fluoride and OH group densities in the test sample, and the pulse width of the pulsed excimer laser.

4. The method according to claim 1, wherein the first irradiation energy density of the pulsed excimer laser beam is within about 0.01 mJ/cm$^2$ per pulse to about 10,000 mJ/cm$^2$ per pulse, and wherein the second irradiation energy density of the pulsed excimer laser beam is within about 0.00001 mJ/cm$^2$ per pulse to about 100 mJ/cm$^2$ per pulse.

5. The method according to claim 4, wherein the step of deriving the first correlation equation further includes the step of correcting the first correlation equation in accordance with a coefficient which is statistically derived to represent effects of structural factors of the test sample, fluoride and OH group densities in the test sample, and the pulse width of the pulsed excimer laser.

6. The method according to claim 4, wherein the optical member is silica glass.

7. The method according to claim 1, wherein the optical member is silica glass.

8. The method according to claim 7, wherein the step of deriving the first correlation equation further includes the step of correcting the first correlation equation in accordance with a coefficient which is statistically derived to represent effects of structural factors of the test sample, fluoride and OH group densities in the test sample, and the pulse width of the pulsed excimer laser.

9. A method of selecting a silica glass optical member among various silica glass optical members, the method comprising the steps of:

estimating durability of each of the silica glass optical members using the method according to claim 4; and selecting the silica glass optical member that has the absorption coefficient corresponding to a transmittance loss of 3%/cm or less with respect to the pulsed excimer laser beam having the second irradiation energy density.

10. A method for estimating durability of an optical member against pulsed excimer laser beam irradiation, the method comprising the steps of:

(a) irradiating a test sample for the optical member with a pulsed excimer laser beam to induce changes in transparency of the test sample with respect to the pulsed excimer laser beam, the irradiation being performed for such a time period as to cover not only a linear region where the changes in transparency changes substantially linearly with the cumulative number of the excimer laser pulses, but also a saturation region where the changes in transparency are substantially saturated to a saturated value, which occurs after the linear region;

(b) measuring changes in the transparency of the test sample with respect to the pulsed excimer laser beam as a function of the cumulative number of the excimer laser pulses that have irradiated the test sample in step (a), the measurement being conducted in both the linear region and the saturated region;

(c) repeating steps (a) and (b) with a plurality of different first predetermined energy densities of the pulsed excimer leer beam to derive a correlation equation representing the changes in the transparency of the test sample in the linear region and the saturated region in terms of the energy density of the pulsed excimer laser beam and the cumulative number of the excimer laser pulses;

(d) inputting the value of an energy density of the pulsed excimer laser beam corresponding to actual usage conditions of the optical member into the correlation equation to derive expected changes in the transparency of the optical member as a function of the cumulative number of the excimer laser pulses under the actual usage conditions; and (e) comparing the expected changes in the transparency derived in step (d) with a required transparency of the optical member to estimate the life-span of the optical member within which the optical member can satisfy the required transparency.

11. The method according to claim 10, wherein the transparency is expressed in terms of a bulk absorption coefficient.

12. The method according to claim 10, wherein step (c) further includes repeating steps (a) and (b) with a plurality of test samples different from each other in at least one of hydrogen and chlorine concentrations therein to derive the correlation equation including dependency of the changes in the transparency on the at least one of the hydrogen and chlorine concentrations, and wherein step (d) further includes inputting the value of the at least one of the hydrogen and chlorine concentrations in the optical member the life span of which is to be estimated to derive the expected changes in the transparency corresponding to the at least one of the hydrogen and chlorine concentrations in the optical member.

13. The method according to claim 10, wherein step (c) further includes repeating steps (a) and (b) with a plurality of test samples different from each other in at least one of a fluorine concentration, an OH group concentration, and an Si—O—Si primary structural factor to derive the correlation equation including dependency of the changes in the transparency on the at least one of the fluorine concentration, the OH group concentration, and the Si—O—Si primary structural factor, and wherein step (d) further includes inputting the value of the at least one of the fluorine concentration, the OH group concentration, and the Si—O—Si primary structural factor in the optical member to derive the expected changes in the transparency corresponding to the at least one of the fluorine concentration, the OH group concentration, and the Si—O—Si primary structural factor in the optical member.

14. The method according to claim 10, wherein step (c) further includes repeating steps (a) and (b) with a plurality of pulsed excimer laser beams having different pulse widths to derive the correlation equation including dependency of the changes in the transparency on the pulse width of the pulsed excimer laser beam, and wherein step (d) further includes inputting the value of a pulse width of the pulsed excimer laser beam corresponding to the actual usage conditions of the optical member into the correlation equation to derive the expected changes in the transparency of the optical member under the actual usage conditions.

15. The method according to claim 10, wherein step (c) includes deriving a linear region correlation equation and a saturated region correlation equation, the linear region correlation equation representing the changes in the transparency of the test sample in the linear region in terms of the energy density of the pulsed excimer laser beam and the cumulative number of the excimer laser pulses, the saturated region correlation equation representing the saturated value of the transparency in terms of the energy density of the pulsed excimer laser beam.

16. The method according to claim 15, wherein step (c) further includes applying the least squares method separately to the linear region and to the saturated region to approximate linear region data measured in step (b) with a substantially linear equation with respect to the cumulative number of the excimer laser pulses to drive the linear region equation and to approximate saturated region data measured in step (b) with a substantially constant value independent of the cumulative number of the excimer laser pulses to derive the saturated region correlation equation.

17. The method according to claim 10, wherein the plurality of different first predetermined energy densities of the pulsed excimer laser beams in step (c) is within the range of about 0.01 mJ/cm$^2$ per pulse to about 10,000 mJ/cm$^2$ per pulse, and wherein the value of the energy density of the pulsed excimer laser beam corresponding to the actual usage conditions of the optical member in step (d) is within the range of about 0.00001 mJ/cm$^2$ per pulse to about 100 mJ/cm$^2$ per pulse.

18. The method according to claim 10, further including the steps of:

providing an silica glass ingot; and cutting out the test sample and the optical member from the silica glass ingot.

19. A method for estimating durability of an optical member against pulsed excimer laser beam irradiation, the method comprising the steps of:

(a) irradiating a test sample for the optical member with a pulsed excimer laser beam to induce changes in transparency of the test sample with respect to the pulsed excimer laser beam, the irradiation being performed for such a time period as to cover not only a linear region and a saturation region;

(b) measuring changes in the transparency of the test sample with respect to the pulsed excimer laser beam as a function of the cumulative number of the excimer laser pulses that have irradiated the test sample in step (a);

(c) repeating steps (a) and (b) with a plurality of different first predetermined energy densities of the pulsed excimer laser beam to derive a correlation equation representing the changes in the transparency of the test sample in the linear region and the saturated region in terms of the energy density of the pulsed excimer laser beam and the cumulative number of the excimer laser pulses; and (d) estimating the durability of the optical member under actual usage conditions using the derived correlation equation.

* * * * *